(12) United States Patent
Samaia Pacheco et al.

(10) Patent No.: US 9,149,421 B1
(45) Date of Patent: Oct. 6, 2015

(54) LIQUID ADHESIVE FOR NAIL POLISH

(71) Applicants: Andreina Samaia Pacheco, Frisco, TX (US); Mark Landis, Frisco, TX (US)

(72) Inventors: Andreina Samaia Pacheco, Frisco, TX (US); Mark Landis, Frisco, TX (US)

(73) Assignee: Mini Mani Moo, LLC, Frisco, TX (US)

( * ) Notice: Subject to any disclaimer, the term of this patent is extended or adjusted under 35 U.S.C. 154(b) by 0 days.

(21) Appl. No.: 14/687,736

(22) Filed: Apr. 15, 2015

Related U.S. Application Data

(60) Provisional application No. 62/094,499, filed on Dec. 19, 2014.

(51) Int. Cl.

| | |
|---|---|
| *A61K 47/32* | (2006.01) |
| *A61K 8/72* | (2006.01) |
| *A61Q 3/02* | (2006.01) |
| *A45D 29/00* | (2006.01) |
| *A61K 8/19* | (2006.01) |
| *A61K 8/46* | (2006.01) |
| *A61K 8/27* | (2006.01) |
| *A61K 8/81* | (2006.01) |
| *A61K 8/92* | (2006.01) |
| *A61Q 3/00* | (2006.01) |

(52) U.S. Cl.
CPC ............... *A61K 8/72* (2013.01); *A45D 29/004* (2013.01); *A61K 8/19* (2013.01); *A61K 8/27* (2013.01); *A61K 8/46* (2013.01); *A61K 8/8141* (2013.01); *A61K 8/92* (2013.01); *A61Q 3/00* (2013.01)

(58) Field of Classification Search
CPC ............. A61K 8/72; A61K 8/19; A61K 8/92; A61K 8/8141; A61K 8/27; A61K 8/46; A61Q 3/00; A45D 29/00; A45D 29/001; A45D 29/004
See application file for complete search history.

(56) References Cited

U.S. PATENT DOCUMENTS

| | | | | |
|---|---|---|---|---|
| 4,126,144 | A * | 11/1978 | Duarte | 132/73 |
| 2010/0116284 | A1 * | 5/2010 | Smith | 132/200 |
| 2012/0160258 | A1 * | 6/2012 | Cruz et al. | 132/201 |

* cited by examiner

*Primary Examiner* — Abigail Fisher

(57) ABSTRACT

A liquid adhesive for nail polish is a topical composition that is used to facilitate the application and removal of nail polish as well as the creation of intricate nail polish designs. The composition features a quantity of rubber latex, a quantity of water, an antiseptic composition of a quantity of ammonium hydroxide and a quantity of thiram, a preserving composition of a quantity of zinc oxide, an aromatic agent, a coloring agent, and a moisturizing agent. The quantity of rubber latex forms a liquid-impermeable coating on the surface of the user's skin or nail once applied. This allows a dried coating of the present invention to be peeled from the skin or nail along with any nail polish applied over the coating. The composition additionally exhibits antimicrobial and antifungal properties as well as a resistance to decomposition and other unwanted chemical and physical changes.

16 Claims, 7 Drawing Sheets

Liquid Adhesive for Nail Polish

- Rubber Latex
- Water
- Antiseptic Composition
- Preserving Composition
- Aromatic Agent
- Coloring Agent
- Moisturizing Agent

FIG. 1

Antiseptic Composition

Ammonium Hydroxide Thiram

FIG. 2

Preserving Composition

Zinc Oxide

FIG. 3

| | |
|---|---|
| Rubber Latex (65.2%) | Water (25.6%) |
| | Thiram (0.1%) |
| | Zinc Oxide (5.5%) |
| | Liquid Fragrance (0.8%) |
| | Acrylic Paint (1.2%) |
| | Oil (0.8%) |

FIG. 7

LIQUID ADHESIVE FOR NAIL POLISH

The current application claims a priority to the U.S. Provisional Patent application Ser. No. 62/094,499 filed on Dec. 19, 2014.

FIELD OF THE INVENTION

The present invention relates generally to a cosmetic product primarily for use with nail polish. More specifically, the present invention is a liquid adhesive for nail polish that allows the user to reduce mess when applying nail polish, create intricate designs with nail polish, and easily remove nail polish as well.

BACKGROUND OF THE INVENTION

The cost of a professional manicure or pedicure can often be exorbitant. As such, the best alternative for those who do not wish to spend the time and money required for a professional manicure or pedicure is to apply the nail polish themselves. Because most people do not possess the skills or dexterity required to create intricate nail polish designs, these attempts often result in messy designs with nail polish mistakenly applied to the cuticle rather than solely on the nail. Additionally, the lack of skills and dexterity required generally results in mediocre nail polish designs when compared to professional manicures or pedicures.

The present invention is a liquid adhesive for nail polish that facilitates the process of applying nail polish as well as preparation prior to applying nail polish and the removal of nail polish. The present invention may be applied to the cuticle around a nail in order to form a barrier and prevent nail polish from accidentally being applied to the skin. The present invention may be easily removed by peeling the present invention off of the skin. Additionally, the present invention may be applied on top of a nail, allowing the use of multiple layers of nail polish in the creation of intricate nail polish designs.

BRIEF DESCRIPTION OF THE DRAWINGS

FIG. 1 is a block diagram depicting the ingredient composition of the present invention.

FIG. 2 is a block diagram depicting the ingredient composition of the antiseptic composition within the preferred embodiment of the present invention.

FIG. 3 is a block diagram depicting the ingredient composition of the preserving composition within the present invention.

FIG. 7 is a block diagram depicting the weight ratios of the ingredient composition in the preferred embodiment of the present invention.

DETAIL DESCRIPTIONS OF THE INVENTION

Figure 4:
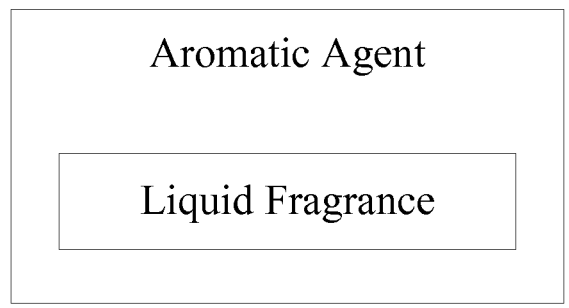
FIG. 4 is a block diagram depicting the ingredient composition of the aromatic agent within the present invention.

All illustrations of the drawings are for the purpose of describing selected versions of the present invention and are not intended to limit the scope of the present invention.

Figure 3:
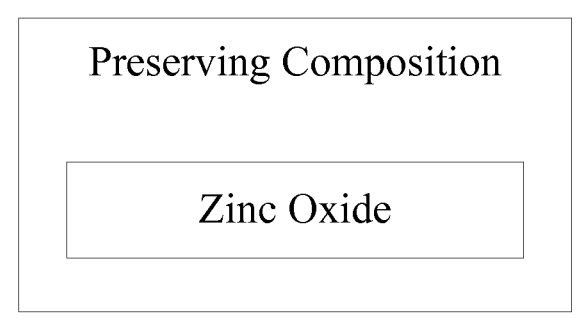

The present invention is a liquid adhesive for nail polish that allows the user to more easily apply nail polish as well as facilitates the creation of intricate nail polish designs and the process of removing nail polish. With reference to FIGS. 1-6, the present invention comprises a quantity of rubber latex, a quantity of water, an antiseptic composition, a preserving composition, an aromatic agent, a coloring agent, and a moisturizing agent. The specific weight ratios of the present invention in the preferred embodiment of the present invention are shown in FIG. 7.

Again with reference to FIG. 1 and FIG. 7, the quantity of rubber latex serves to provide a liquid-impermeable coating on the surface of the user's skin as well as the surface of the user's nail once applied. Once the present invention has been applied to the user's skin or nail in liquid form, the present invention is able to dry. Upon drying, the quantity of rubber latex forms a coating upon the user's skin or nail that is liquid-impermeable. This allows the user to apply nail polish onto an uncoated portion of nail. The coating provided by the present invention prevents any accidental application of nail polish onto the user's skin or any portions of the nail upon which the user does not wish to apply nail polish. When the user has finished applying nail polish, the quantity of rubber latex allows the user to simply peel the coating provided by the present invention off of the skin or nail. In the preferred embodiment of the present invention, the quantity of rubber latex is approximately 65.2% wt. of the liquid adhesive for nail polish.

The quantity of water allows the present invention to maintain a liquid form prior to application to the user's nail. The present invention is primarily intended for application utilizing a brush or similar device. The quantity of liquid water maintains the liquid form of the present invention until applied. Upon exposure to air, the present invention is able to dry. In the preferred embodiment of the present invention, the quantity of water is approximately 25.6% wt. of the liquid adhesive for nail polish.

Referring again to FIG. 2 and FIG. 7, the antiseptic composition provides various antiseptic, antimicrobial, and antifungal properties to the present invention. In the preferred embodiment of the present invention, the antiseptic composition comprises a quantity of ammonium hydroxide and a quantity of thiram. The quantity of ammonium hydroxide is a solution of ammonia and water that is used in low concentrations in cosmetic applications. The quantity of ammonium hydroxide provides disinfecting properties to the portions of the user's skin or nail to which the present invention is applied. Additionally, the quantity of ammonium hydroxide further allows the present invention to maintain liquid form prior to application to the user's skin or nail. In the preferred embodiment of the present invention, the quantity of ammonium hydroxide is approximately 0.9% wt. of the liquid adhesive for nail polish. The quantity of thiram provides antifungal and bactericidal properties to the user's skin or nail when the present invention is applied. In the preferred embodiment of the present invention, the quantity of thiram is approximately 0.1% wt. of the liquid adhesive for nail polish. Similar to the quantity of ammonium hydroxide, the quantity of thiram is utilized in low concentrations in cosmetic applications. In the preferred embodiment of the present invention, the quantity of thiram is present in powder, granule, or similar water-soluble form.

Again with reference to FIG. 3 and FIG. 7, the preserving composition preserves the present invention against decomposition, infections, and spoilage, as well as additional undesirable chemical and physical changes. In the preferred embodiment of the present invention, the preserving composition comprises a quantity of zinc oxide. The quantity of zinc oxide is able to improve the overall microbiological quality of the present invention, greatly improving the shelf life of the present invention as well as preventing contamination of the present invention. The quantity of zinc oxide additionally provides antimicrobial and antifungal properties to the present invention. In the preferred embodiment of the present invention, the quantity of zinc oxide is approximately 5.5% wt. of the liquid adhesive for nail polish.

The aromatic agent serves to provide a pleasant scent to the present invention. As shown in FIG. 4, in the preferred embodiment of the present invention, the aromatic agent comprises a quantity of liquid fragrance. The present invention is not limited with respect to the specific type of scent provided to the present invention nor with respect to the specific type of the quantity of liquid fragrance. For example, the quantity of liquid fragrance may be an essential oil containing aroma compounds that has been extracted from seeds, flowers, leaves, roots, stems, or bark of plants. Alternatively, the quantity of liquid fragrance may be a synthetic aroma chemical. The quantity of liquid fragrance further aids in maintaining the liquid form of the present invention. In the preferred embodiment of the present invention, the quantity of liquid fragrance is approximately 0.8% wt. of the liquid adhesive for nail polish as shown in FIG. 7.

Figure 5:
FIG. 5 is a block diagram depicting the ingredient composition of the coloring agent within the present invention.
Figure 6:
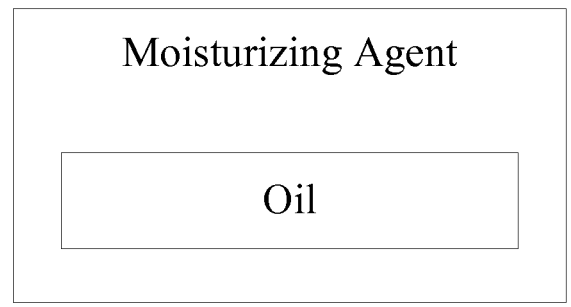
FIG. 6 is a block diagram depicting the ingredient composition of the moisturizing agent within the present invention.

The coloring agent improves the aesthetic appearance of the present invention. As shown in FIG. 5, in the preferred embodiment of the present invention, the coloring agent comprises a quantity of acrylic paint. Similar to the quantity of liquid fragrance, the present invention is not limited with respect to the specific color of the quantity of acrylic paint. Additionally, the quantity of acrylic paint further aids in maintaining the liquid form of the present invention. In the preferred embodiment of the present invention, the quantity of acrylic paint is approximately 1.2% wt. of the liquid adhesive for nail polish as shown in FIG. 7

Again with reference to FIG. 6 and FIG. 7, the moisturizing agent provides moisturizing properties when applied to the user's skin. This is particularly effective when the present invention is applied to the user's cuticle as the moisturizing properties provided by the moisturizing agent are able to minimize the possibilities of hangnails and similar issues related to dry skin. In the preferred embodiment of the present invention, the moisturizing agent comprises a quantity of oil. The quantity of oil moisturizes and otherwise nourishes the user's skin when applied to the user's cuticle. In the preferred embodiment of the present invention, the quantity of oil is approximately 0.8% wt. of the liquid adhesive for nail polish.

The present invention has three primary applications in the application of nail polish:

1. The present invention may be applied to the cuticle surrounding the user's nail prior to the application of nail polish. The present invention is initially applied in liquid form and allowed to dry. When the present invention has been allowed to dry on the user's skin, the quantity of rubber latex forms a liquid-impermeable barrier on the user's skin. This prevents nail polish from being accidentally applied to the user's skin as the nail polish is unable to come into contact with the skin. The user is then able to apply nail polish to the surface of the nail as normal. Once dry, the present invention may simply be peeled from the skin, removing any nail polish applied on top of the coating provided by the present invention as well.
2. The present invention facilitates the removal of nail polish without the need for nail polish remover. The user is able to apply a coating of the present invention to the surface of a nail. Nail polish may then be applied as normal onto the coating of the present invention. When the user wishes to remove the nail polish, the coating of the present invention may be peeled off, removing the nail polish applied on top of the coating as well.
3. The present invention facilitates the creation of intricate nail polish designs. A first coating of nail polish is first applied to the entire surface of a nail. Once the first coating of nail polish has dried, a coating of the present invention is then applied onto the first coating of nail polish on the portions of the nail that the user does not wish to be coated by a second coating of nail polish. The coating of the present invention is allowed to dry. A second coating of nail polish is then applied over the entire surface of the nail and is allowed to dry. The coating of the present invention may then be peeled off and removed from the nail, leaving behind the first coating of nail polish and the second coating of nail polish on the user's nail in the applied design.

Although the present invention has been explained in relation to its preferred embodiment, it is understood that many other possible modifications and variations can be made without departing from the spirit and scope of the present invention as hereinafter claimed.

What is claimed is:

1. A liquid adhesive for nail polish comprises:
   a quantity of rubber latex being approximately 65.2% wt. of the liquid adhesive for nail polish;
   a quantity of water being a proximately 25.6% wt. of the liquid adhesive for nail polish;
   an antiseptic composition;
   a preserving composition;
   an aromatic agent;
   a coloring agent; and
   a moisturizing agent.

2. The liquid adhesive for nail polish as claimed in claim 1, wherein the antiseptic composition comprises a quantity of ammonium hydroxide.

3. The liquid adhesive for nail polish as claimed in claim 2, wherein the quantity of ammonium hydroxide is approximately 0.9% wt. of the liquid adhesive for nail polish.

4. The liquid adhesive for nail polish as claimed in claim 1, wherein the antiseptic composition comprises a quantity of thiram.

5. The liquid adhesive for nail polish as claimed in claim 4, wherein the quantity of thiram is approximately 0.1% wt. of the liquid adhesive for nail polish.

6. The liquid adhesive for nail polish as claimed in claim 1, wherein the preserving composition comprises a quantity of zinc oxide.

7. The liquid adhesive for nail polish as claimed in claim 6, wherein the quantity of zinc oxide is approximately 5.5% wt. of the liquid adhesive for nail polish.

8. The liquid adhesive for nail polish as claimed in claim 1, wherein the aromatic agent comprises a quantity of liquid fragrance.

9. The liquid adhesive for nail polish as claimed in claim 8, wherein the quantity of liquid fragrance is approximately 0.8% wt. of the liquid adhesive for nail polish.

10. The liquid adhesive for nail polish as claimed in claim 1, wherein the coloring agent comprises a quantity of acrylic paint.

11. The liquid adhesive formula for nail polish as claimed in claim 10, wherein the quantity of acrylic paint is approximately 1.2% wt. of the liquid adhesive for nail polish.

12. The liquid adhesive for nail polish as claimed in claim 1, wherein the moisturizing agent comprises a quantity of oil.

13. The liquid adhesive for nail polish as claimed in claim 12, wherein the quantity of oil is approximately 0.8% wt. of the liquid adhesive for nail polish.

14. A liquid adhesive for nail polish comprises:
   a quantity of rubber latex being approximately 65.2% wt. of the liquid adhesive for nail polish;
   a quantity of water being approximately 25.6% wt. of the liquid adhesive for nail polish;
   an antiseptic composition;
   a preserving composition;
   an aromatic agent;
   a coloring agent; and
   a moisturizing agent wherein:
      the antiseptic composition comprises a quantity of ammonium hydroxide and a quantity of thiram;
      the preserving composition comprises a quantity of zinc oxide;
      the aromatic agent comprises a quantity of liquid fragrance;
      the coloring agent comprises a quantity of acrylic paint; and
      the moisturizing agent comprises a quantity of oil.

15. The liquid adhesive for nail polish as claimed in claim 14, wherein:
   the quantity of ammonium hydroxide is approximately 0.9% wt. of the liquid adhesive for nail polish;
   the quantity of thiram is approximately 0.1% wt. of the liquid adhesive for nail polish;
   the quantity of zinc oxide is approximately 5.5% wt. of the liquid adhesive for nail polish;
   the quantity of liquid fragrance is approximately 0.8% wt. of the liquid adhesive for nail polish;
   the quantity of acrylic paint is approximately 1.2% wt. of the liquid adhesive for nail polish; and
   the quantity of oil is approximately 0.8% wt. of the liquid adhesive for nail polish.

16. The liquid adhesive for nail polish as claimed in claim 14, wherein: the quantity of ammonium hydroxide is approximately 0.9% wt. of the liquid adhesive for nail polish; the quantity of thiram is approximately 0.1% wt, of the liquid adhesive for nail polish; and the quantity of zinc oxide is approximately 5.5% wt. of the liquid adhesive for nail polish.

* * * * *